United States Patent
Gan et al.

(10) Patent No.: US 6,692,865 B2
(45) Date of Patent: Feb. 17, 2004

(54) DOUBLE CURRENT COLLECTOR CATHODE DESIGN USING MIXTURES OF TWO ACTIVE MATERIALS FOR ALKALI METAL OR ION ELECTROCHEMICAL CELLS

(75) Inventors: Hong Gan, East Amherst, NY (US); Esther S. Takeuchi, East Amherst, NY (US)

(73) Assignee: Wilson Greatbatch Ltd., Clarence, NY (US)

( * ) Notice: Subject to any disclaimer, the term of this patent is extended or adjusted under 35 U.S.C. 154(b) by 268 days.

(21) Appl. No.: 10/008,823

(22) Filed: Oct. 24, 2001

(65) Prior Publication Data

US 2002/0090548 A1 Jul. 11, 2002

Related U.S. Application Data

(60) Provisional application No. 60/249,688, filed on Nov. 17, 2000.

(51) Int. Cl.[7] .............................. H01M 4/00; H01M 4/48
(52) U.S. Cl. ........................ 429/128; 429/219; 429/220; 429/221; 429/223; 429/224; 429/231.1; 429/231.3; 429/231.5; 429/231.7; 429/245; 429/330; 429/328; 429/332; 429/336; 429/231.95
(58) Field of Search ........................... 429/231.95, 219, 429/231.5, 220, 221, 223, 224, 231.7, 245, 231.3, 231.1, 330, 128, 328, 332, 336

(56) References Cited

U.S. PATENT DOCUMENTS

| | | |
|---|---|---|
| 3,520,729 A | 7/1970 | Voss et al. |
| 4,161,063 A | 7/1979 | Goebel et al. |
| 4,292,357 A | 9/1981 | Erisman et al. |
| 4,324,828 A | 4/1982 | Ebato et al. |
| 4,409,730 A | 10/1983 | Goebel |
| 4,439,916 A | 4/1984 | Faber |
| 5,180,642 A | 1/1993 | Weiss et al. |
| 5,571,636 A | 11/1996 | Ohta et al. |
| 5,582,935 A | 12/1996 | Dasgupta et al. |
| 5,639,568 A | 6/1997 | Pedicini et al. |
| 5,658,694 A | 8/1997 | Charkey |
| 5,667,916 A | 9/1997 | Ebel et al. |
| 5,670,276 A | 9/1997 | Takeuchi et al. |
| 5,716,422 A | 2/1998 | Muffoletto et al. |
| 5,744,258 A | 4/1998 | Bai et al. |
| 5,863,676 A | 1/1999 | Charkey et al. |
| 5,993,999 A | 11/1999 | Rivers et al. |
| 6,551,747 B1 * | 4/2003 | Gan ........................... 429/245 |

* cited by examiner

*Primary Examiner*—Laura Weiner
(74) *Attorney, Agent, or Firm*—Michael F. Scalise

(57) ABSTRACT

A new sandwich cathode design is provided having a first cathode structure of a first cathode active material of a relatively low energy density but of a relatively high rate capability, for example SVO, mixed with a second cathode active material having a relatively high energy density but a relatively low rate capability, for example $CF_x$, with the percentage of SVO being less than that of $CF_x$ and sandwiched between two current collectors. Then, a second cathode mixture of SVO and $CF_x$ active materials is contacted to the outside of the current collectors. However, the percentage of SVO to $CF_x$ is greater in the second structure than in the first. Such an exemplary cathode design might look like:

(100−y)% SVO+y% $CF_x$, wherein $0 \leq y \leq 100$/current collector/(100−x)% SVO+x% $CF_x$, wherein $0 \leq x \leq 100$/current collector/(100−y)% SVO+y% $CF_x$, wherein $0 \leq y \leq 100$, and wherein the ratio of x to y is selected from the group consisting of y<x, x<y and x=y.

50 Claims, No Drawings

DOUBLE CURRENT COLLECTOR CATHODE DESIGN USING MIXTURES OF TWO ACTIVE MATERIALS FOR ALKALI METAL OR ION ELECTROCHEMICAL CELLS

CROSS REFERENCE TO RELATED APPLICATION

This application claims priority based on provisional application Ser. No. 60/249,688, filed Nov. 17, 2000.

BACKGROUND OF THE INVENTION

1. Field of Invention

This invention relates to the conversion of chemical energy to electrical energy. In particular, the present invention relates to a new sandwich cathode design having two cathode active materials provided in two different mixtures. The first cathode active material is of a relatively low energy density but of a relatively high rate capability while the second cathode active material has a relatively high energy density but a relatively low rate capability. The cathode is built in a sandwich configuration having a first cathode structure sandwiched between two current collectors. Then, a second cathode structure is provided in contact with at least the other side of one of the current collectors, and preferably facing the anode. In each of the first and second cathode structures, the weight percent of the first and second active materials equals 100. For example, the first cathode structure has, by weight: $(100-y)\%$ first cathode active material+$y\%$ second cathode active material, where $0 \leq y \leq 100$, and the second cathode structure has: $(100-x)\%$ first cathode active material+$x\%$ second cathode active material, where $0 \leq x \leq 100$, and wherein x<y, y<x or x=y.

The present cathode design is useful in applications where a premium is places on increased energy density, such as in power sources associated with implantable medical devices, while providing relative safety under short circuit conditions.

2. Prior Art

The capacity of an electrochemical cell is not only dependent on the electrode assembly design and packing efficiency, it is also dependent on the type of active materials used. For example, it is generally recognized that for lithium cells, silver vanadium oxide (SVO) and, in particular, $\epsilon$-phase silver vanadium oxide ($AgV_2O_{5.5}$), is preferred as the cathode active material. This active material has a theoretical volumetric capacity of 1.37 Ah/ml. By comparison, the theoretical volumetric capacity of $CF_x$ material (x=1.1) is 2.42 Ah/ml, which is 1.77 times that of $\epsilon$-phase silver vanadium oxide.

An attempt to use high capacity materials, such as $CF_x$, by mixing it with a high rate cathode material, such as SVO, is reported in U.S. Pat. No. 5,180,642 to Weiss et. al. However, electrochemical cells made from such cathode composites have lower rate capability. Increasing the cell's theoretical capacity by using $CF_x$ as part of the cathode mix is in part canceled by lowering of its power capability in a high rate discharge application.

U.S. Pat. No. 5,614,331 to Takeuchi et al., which is assigned to the assignee of the present invention and incorporated hereby by reference, describes a method of using a medium rate $CF_x$ cell to power the circuitry of an implantable defibrillator while simultaneously using a SVO cell to provide the power supply under high rate applications for the device. The advantage of this method is that all of the high power SVO energy is reserved for the high power application such as charging a capacitor while the device monitoring function, for example for monitoring the heart beat, which requires generally low power requirements, is provided by the high capacity $CF_x$ system. However, this battery construction requires a very careful design to balance the capacities of the high power cell (SVO) and the low power cell ($CF_x$) with both cells reaching end of service life at or near the same time. Such a balance, nevertheless, is very difficult to achieve due to the variable device usage requirements of a particular patient.

SUMMARY OF THE INVENTION

Accordingly, the object of the present invention is to improve the performance of lithium electrochemical cells by providing a new concept in electrode design. The new electrode configuration is especially useful in applications where increased energy density is desired while providing relative safety under short circuit conditions. Also, the cell has a predictable end of life, which is useful for scheduling cell replacement procedures, such as in implantable medical device applications.

To fulfill these needs, a new sandwich cathode design is provided having a first cathode structure of a first cathode active material of a relatively low energy density but of a relatively high rate capability, for example SVO, mixed with a second cathode active material having a relatively high energy density but a relatively low rate capability, for example $CF_x$, with the percentage of SVO being less than that of $CF_x$ and sandwiched between two current collectors. Then, a second cathode mixture of SVO and $CF_x$ active materials is contacted to the outside of the current collectors. However, the percentage of SVO to $CF_x$ is greater in the second structure than in the first. Such an exemplary cathode design might look like, by weight:

$(100-y)\%$ SVO+$y\%$ $CF_x$, wherein $0 \leq y \leq 100$/current collector/$(100-x)\%$ SVO+$x\%$ $CF_x$, wherein $0 \leq x \leq 100$/current collector/$(100-y)\%$ SVO+$y\%$ $CF_x$, wherein $0 \leq y \leq 100$, and wherein y<x, x<y or x=y.

These and other objects of the present invention will become increasingly more apparent to those skilled in the art by reference to the following description.

DETAILED DESCRIPTION OF THE PREFERRED EMBODIMENTS

An electrochemical cell according to the present invention comprises an anode of a metal selected from Groups IA, IIA and IIIB of the Periodic Table of the Elements. Such anode active materials include lithium, sodium, potassium, etc., and their alloys and intermetallic compounds including, for example, Li—Si, Li—Al, Li—B, Li—Mg, and Li—Si—B alloys and intermetallic compounds. The preferred anode comprises lithium. An alternate anode comprises a lithium alloy such as a lithium-aluminum alloy. The greater the amount of aluminum present by weight in the alloy, however, the lower the energy density of the cell.

The form of the anode may vary, but preferably the anode is a thin metal sheet or foil of the anode metal, pressed or rolled on a metallic anode current collector, i.e., preferably comprising titanium, titanium alloy or nickel, to form an anode component. Copper, tungsten and tantalum are also suitable materials for the anode current collector. In the exemplary cell of the present invention, the anode component has an extended tab or lead of the same material as the anode current collector, i.e., preferably nickel or titanium, integrally formed therewith such as by welding and contacted by a weld to a cell case of conductive metal in a case-negative electrical configuration. Alternatively, the anode may be formed in some other geometry, such as a bobbin shape, cylinder or pellet to allow an alternate low surface cell design.

The electrochemical cell of the present invention further comprises a cathode of electrically conductive materials which serve as the other electrode of the cell. The cathode is preferably of solid materials and the electrochemical reaction at the cathode involves conversion of ions which migrate from the anode to the cathode into atomic or molecular forms. The solid cathode may comprise a first active material of a carbonaceous chemistry and a second active material of a metal element, a metal oxide, a mixed metal oxide and a metal sulfide, and combinations thereof. The metal oxide, the mixed metal oxide and the metal sulfide of the second active material have a relatively lower energy density but a relatively higher rate capability than the first carbonaceous active material.

In that respect the first active material is of a relatively high energy density and a relatively low rate capability in comparison to the second cathode active material. The first active material is preferably a carbonaceous compound prepared from carbon and fluorine, which includes graphitic and nongraphitic forms of carbon, such as coke, charcoal or activated carbon. Fluorinated carbon is represented by the formula $(CF_x)_n$ wherein x varies between about 0.1 to 1.9 and preferably between about 0.5 and 1.2, and $(C_2F)_n$ wherein n refers to the number of monomer units which can vary widely.

The sandwich cathode design of the present invention further includes a second active material formed by the chemical addition, reaction, or otherwise intimate contact of various metal oxides, metal sulfides and/or metal elements, preferably during thermal treatment, sol-gel formation, chemical vapor deposition or hydrothermal synthesis in mixed states. The active materials thereby produced contain metals, oxides and sulfides of Groups IB, IIB, IIIB, IVB, VB, VIB, VIIB and VIII, which include the noble metals and/or other oxide and sulfide compounds. A preferred second cathode active material is a reaction product of at least silver and vanadium.

One preferred mixed metal oxide is a transition metal oxide having the general formula $SM_xV_2O_y$ where SM is a metal selected from Groups IB to VIIB and VIII of the Periodic Table of Elements, and wherein x is about 0.30 to 2.0 and y is about 4.5 to 6.0 in the general formula. By way of illustration, and in no way intended to be limiting, one exemplary cathode active material comprises silver vanadium oxide having the general formula $Ag_xV_2O_y$ in any one of its many phases, i.e., β-phase silver vanadium oxide having in the general formula x=0.35 and y=5.8, γ-phase silver vanadium oxide having in the general formula x=0.80 and y=5.40 and ε-phase silver vanadium oxide having in the general formula x=1.0 and y=5.5, and combination and mixtures of phases thereof. For a more detailed description of such cathode active materials reference is made to U.S. Pat. No. 4,310,609 to Liang et al., which is assigned to the assignee of the present invention and incorporated herein by reference.

Another preferred composite transition metal oxide cathode material includes $V_2O_z$ wherein $z \leq 5$ combined with $Ag_2O$ having silver in either the silver(II), silver(I) or silver(0) oxidation state and CuO with copper in either the copper(II), copper(I) or copper(0) oxidation state to provide the mixed metal oxide having the general formula $Cu_xAg_yV_2O_z$, (CSVO). Thus, the composite cathode active material may be described as a metal oxide-metal oxide-metal oxide, a metal-metal oxide-metal oxide, or a metal-metal-metal oxide and the range of material compositions found for $Cu_xAg_yV_2O_z$ is preferably about $0.01 \leq z \leq 6.5$. Typical forms of CSVO are $Cu_{0.16}Ag_{0.67}V_2O_z$ with z being about 5.5 and $Cu_{0.5}Ag_{0.5}V_2O_z$ with z being about 5.75. The oxygen content is designated by z since the exact stoichiometric proportion of oxygen in CSVO can vary depending on whether the cathode material is prepared in an oxidizing atmosphere such as air or oxygen, or in an inert atmosphere such as argon, nitrogen and helium. For a more detailed description of this cathode active material reference is made to U.S. Pat. Nos. 5,472,810 to Takeuchi et al. and 5,516,340 to Takeuchi et al., both of which are assigned to the assignee of the present invention and incorporated herein by reference.

In a broader sense, it is contemplated by the scope of the present invention that the first active material of the present sandwich cathode design is any material which has a relatively higher energy density but a relatively lower rate capability than the second active material. In addition to fluorinated carbon, $Ag_2O$, $Ag_2O_2$, $CuF_2$, $Ag_2CrO_4$, $MnO_2$ and even SVO itself are useful as the first active material, and in addition to silver vanadium oxide and copper silver vanadium oxide, $V_2O_5$, $MnO_2$, $LiCoO_2$, $LiNiO_2$, $LiMn_2O_4$, $TiS_2$, $Cu_2S$, FeS, $FeS_2$, copper oxide, copper vanadium oxide, and mixtures thereof are useful as the second active material. In a still broader sense, either of the first and second cathode structures is a mixture of two or three or more of the above active materials, or one of the cathode structures has only a single active material while the other structure has two or more active materials.

The true density and theoretical volumetric capacities of several active materials are listed in Table 1.

TABLE 1

| Material | True Density (g/ml) | Theoretical Capacity (Ah/ml) |
|---|---|---|
| $CF_x$ | 2.70 | 2.42 |
| $Ag_2O_2$ | 7.48 | 3.24 |
| $Ag_2O$ | 7.14 | 1.65 |
| $AgV_2O_{5.5}$ | 4.34 | 1.37 |

The data in Table 1 indicate that $CF_x$, $Ag_2O_2$, $Ag_2O$, all have higher theoretical volumetric capacities than that of SVO. It has also been determined that each of the silver-containing materials listed in Table 1 can be pressed into cohesive pellets that readily adhere to a current collector without the presence of binder and conductive additives. This means that these silver-containing materials are useful as the second active material in sandwich cathode designs according to the present invention. In practice, it is extremely difficult to press electrode materials to their true density, and practical theoretical capacities are less than those listed in Table 1. Table 2 lists the practical densities and practical volumetric capacities of the above cathode materials based on experimental results.

TABLE 2

| Material | Practical Density (g/ml) | % of Theoretical True Density | Practical Capacity (Ah/ml) |
|---|---|---|---|
| $AgV_2O_{5.5}$ (94%) | 3.40* | 78.3 | 1.07 |
| $AgV_2O_{5.5}$ (100%) | 4.10 | 94.5 | 1.29 |
| $CF_x$ (91%) | 1.41* | 52.2 | 1.27 |
| $Ag_2O$ (100%) | 6.57 | 92.0 | 1.52 |
| $Ag_2O_2$ (100%) | 6.01 | 80.3 | 2.62 |

*Practical density of the active materials. The non-active materials including binders and conductive additives.

The data in Table 2 indicate that silver oxide materials provide greater discharge capacity than similar volumes of $CF_x$ and SVO materials. Pure SVO provides 21% more volumetric capacity than a cathode electrode formulation of 94% SVO, 3% PTFE binder and 3% of a conductive diluent. The capacity numbers listed in Table 2 are theoretical values based on complete reduction of each material.

Before fabrication into a sandwich electrode for incorporation into an electrochemical cell according to the present invention, the first and second cathode active materials prepared as described above are preferably mixed with a binder material such as a powdered fluoro-polymer, more preferably powdered polytetrafluoroethylene or powdered polyvinylidene flouride present at about 1 to about 5 weight percent of the cathode mixture. Further, up to about 10 weight percent of a conductive diluent is preferably added to the cathode mixture to improve conductivity. Suitable materials for this purpose include acetylene black, carbon black and/or graphite or a metallic powder such as powdered nickel, aluminum, titanium and stainless steel. The preferred cathode active mixture thus includes a powdered fluoro-polymer binder present at about 3 weight percent, a conductive diluent present at about 3 weight percent and about 94 weight percent of the cathode active material.

Cathode components for incorporation into an electrochemical cell according to the present invention may be prepared by rolling, spreading or pressing the first and second cathode active materials onto a suitable current collector selected from the group consisting of stainless steel, titanium, tantalum, platinum, gold, aluminum, cobalt nickel alloys, highly alloyed ferritic stainless steel containing molybdenum and chromium, and nickel-, chromium-, and molybdenum-containing alloys. The preferred current collector material is titanium, and most preferably the titanium cathode current collector has a thin layer of graphite/carbon paint applied thereto. Cathodes prepared as described above may be in the form of one or more plates operatively associated with at least one or more plates of anode material, or in the form of a strip wound with a corresponding strip of anode material in a structure similar to a "jellyroll".

According to the present invention, $CF_x$ cathode material, which provides a relatively low power or rate capability but a relatively high energy density or volumetric capability, and SVO cathode material, which has a relatively low energy density but a relatively high rate capability, are provided in two different mixtures on opposite sides of a current collector, so that both materials are in direct contact therewith. Therefore, one exemplary cathode plate has a first cathode structure short circuited with a second cathode structure with the following configuration, by weight:
the first cathode structure comprises a first cathode active material in a first percentage of (100−x)% and a second cathode active material in a second percentage of x% and wherein the second cathode structure comprises the first cathode active material in a third percentage of (100−y)% and the second cathode active material in a fourth percentage of y%. The ratio of x to y in the first and second cathode structures is either x<y, y<x or x=y.

One exemplary cathode has the configuration, by weight:
(100−y)% first cathode active material+y% second cathode active material, wherein $0 \leq y \leq 100$/current collector/(100−x)% first cathode active material+x% second cathode active material, wherein $0 \leq x \leq 100$/current collector/(100−y)% first cathode active material+y% second cathode active material, wherein $0 \leq y \leq 100$, and wherein x<y, y<x or x=y.

Another exemplary cathode has the configuration, by weight:
(100−y)% first cathode active material+y% second cathode active material, wherein $0 \leq y \leq 100$/current collector/(100−y)% first cathode active material+y% second cathode active material, wherein $0 \leq y \leq 100$/(100−x)% first cathode active material+x% second cathode active material, wherein $0 \leq x \leq 100$/(100−y)% first cathode active material+y% second cathode active material, wherein $0 \leq y \leq 100$/current collector/(100−y)% first cathode active material+y% second cathode active material, wherein $\leq 0y \leq 100$, and wherein x<y, y<x, or x=y, or (100−y)% first cathode active material+y% second cathode active material, wherein $0 \leq y \leq 100$/first current collector/(100−x)% first cathode active material+x% second cathode active material, wherein $0 \leq x \leq 100$/second current collector/(100−z)% first cathode active material+z% second cathode active material, wherein $0 \leq z \leq 100$, and wherein $y \leq x$ and $z \leq x$ and wherein y<z or y>z, or (100−y)% first cathode active material+y% second cathode active material, wherein $0 \leq y \leq 100$/first current collector/(100−y)% first cathode active material+y% second cathode active material, wherein $0 \leq y \leq 100$/(100−x)% first cathode active material+x% second cathode active material, wherein $0 \leq x \leq 100$/(100−z)% first cathode active material+z% second cathode active material, wherein $0 \leq z \leq 100$/second current collector/(100−z)% first cathode active material+z% second cathode active material, wherein $\leq 0z \leq 100$, and wherein $y \leq x$ and $z \leq x$ and wherein y<z or y>z.

A still further exemplary cathode has the configuration, by weight:
(100−y)% first cathode active material+y% second cathode active material/current collector/(100−x)% first cathode active material+x% second cathode active material, wherein x<y, y<x or x=y.

Specific chemistries may have the following cathode configurations, by weight:
(100−y)% SVO+y% $CF_x$, wherein $0 \leq y \leq 100$/current collector/(100−x)% SVO+x% $CF_x$, wherein $0 \leq x \leq 100$/current collector/(100−y)% SVO+y% $CF_x$, wherein $0 \leq y \leq 100$, and wherein y<x, x<y or x=y, or (100−y)% SVO+y% $CF_x$, wherein $0 \leq y \leq 100$/current collector/(100−y)% SVO+y% $CF_x$, wherein $0 \leq y \leq 100$/(100−x)% SVO+x% $CF_x$, wherein $0 \leq x \leq 100$/(100−y)% SVO+y% $CF_x$, wherein $0 \leq y \leq 100$/current collector/(100−y)% SVO+y% $CF_x$, wherein $\leq 0y \leq 100$, and wherein y<x, x<y or x=y.

A preferred electrochemical chemistry has a lithium anode and a cathode configuration of, by weight:

(100−y)% SVO+y% $CF_x$/current collector/(100−x)% SVO+x% $CF_x$, wherein y≦x with the (100−y)% SVO+y% $CF_x$ facing the lithium anode.

Another preferred electrochemical chemistry has a lithium anode and a cathode configuration of, by weight: (100−y)% SVO+y% $CF_x$/current collector/(100−x)% SVO+x% $CF_x$, wherein x≦y with the (100−y)% SVO+y% $CF_x$ facing the lithium anode.

Since $CF_x$ material has significantly higher volumetric capacity than that of SVO material, i.e., approximately 1.77 times greater, in order to optimize the final cell capacity, the amount of $CF_x$ material should be maximized and the amount of SVO material used should be minimized to the point that it is still practical in engineering and acceptable in electrochemical performance.

Further, end of service life indication is the same as that of a standard Li/SVO cell. And, it has been determined that the SVO electrode material and the $CF_x$ electrode material according to the present invention reach end of life at the same time. This is the case regardless of the use of the cell. Since both electrode materials reach end of service life at the same time, no energy capacity is wasted.

In order to prevent internal short circuit conditions, the sandwich cathode is separated from the Group IA, IIA or IIIB anode by a suitable separator material. The separator is of electrically insulative material, and the separator material also is chemically unreactive with the anode and cathode active materials and both chemically unreactive with and insoluble in the electrolyte. In addition, the separator material has a degree of porosity sufficient to allow flow there through of the electrolyte during the electrochemical reaction of the cell. Illustrative separator materials include fabrics woven from fluoropolymeric fibers including polyvinylidine fluoride, polyethylenetetrafluoroethylene, and polyethylenechlorotrifluoroethylene used either alone or laminated with a fluoropolymeric microporous film, non-woven glass, polypropylene, polyethylene, glass fiber materials, ceramics, polytetrafluoroethylene membrane commercially available under the designation ZITEX (Chemplast Inc.), polypropylene membrane commercially available under the designation CELGARD (Celanese Plastic Company, Inc.) and a membrane commercially available under the designation DEXIGLAS (C. H. Dexter, Div., Dexter Corp.).

The electrochemical cell of the present invention further includes a nonaqueous, ionically conductive electrolyte which serves as a medium for migration of ions between the anode and the cathode electrodes during the electrochemical reactions of the cell. The electrochemical reaction at the electrodes involves conversion of ions in atomic or molecular forms which migrate from the anode to the cathode. Thus, nonaqueous electrolytes suitable for the present invention are substantially inert to the anode and cathode materials, and they exhibit those physical properties necessary for ionic transport, namely, low viscosity, low surface tension and wettability.

A suitable electrolyte has an inorganic, ionically conductive salt dissolved in a nonaqueous solvent, and more preferably, the electrolyte includes an ionizable alkali metal salt dissolved in a mixture of aprotic organic solvents comprising a low viscosity solvent and a high permittivity solvent. The inorganic, ionically conductive salt serves as the vehicle for migration of the anode ions to intercalate or react with the cathode active materials. Preferably, the ion forming alkali metal salt is similar to the alkali metal comprising the anode.

In the case of an anode comprising lithium, the alkali metal salt of the electrolyte is a lithium based salt. Known lithium salts that are useful as a vehicle for transport of alkali metal ions from the anode to the cathode include $LiPF_6$, $LiBF_4$, $LiAsF_6$, $LiSbF_6$, $LiClO_4$, $LiO_2$, $LiAlCl_4$, $LiGaCl_4$, $LiC(SO_2CF_3)_3$, $LiN(SO_2CF_3)_2$, LiSCN, $LiO_3SCF_3$, $LiC_6F_5SO_3$, $LiO_2CCF_3$, $LiSO_6F$, $LiB(C_6H_5)_4$, $LiCF_3SO_3$, and mixtures thereof.

Low viscosity solvents useful with the present invention include esters, linear and cyclic ethers and dialkyl carbonates such as tetrahydrofuran (THF), methyl acetate (MA), diglyme, trigylme, tetragylme, dimethyl carbonate (DMC), 1,2-dimethoxyethane (DME), 1,2-diethoxyethane (DEE), 1-ethoxy,2-methoxyethane (EME), ethyl methyl carbonate, methyl propyl carbonate, ethyl propyl carbonate, diethyl carbonate, dipropyl carbonate, and mixtures thereof, and high permittivity solvents include cyclic carbonates, cyclic esters and cyclic amides such as propylene carbonate (PC), ethylene carbonate (EC), butylene carbonate, acetonitrile, dimethyl sulfoxide, dimethyl formamide, dimethyl acetamide, γ-valerolactone, γ-butyrolactone (GBL), N-methyl-pyrrolidinone (NMP), and mixtures thereof. In the present invention, the preferred anode is lithium metal and the preferred electrolyte is 0.8M to 1.5M $LiAsF_6$ or $LiPF_6$ dissolved in a 50:50 mixture, by volume, of propylene carbonate as the preferred high permittivity solvent and 1,2-dimethoxyethane as the preferred low viscosity solvent.

The assembly of the cells described herein is preferably in the form of a wound element configuration. That is, the fabricated negative electrode, positive electrode and separator are wound together in a "jellyroll" type configuration or "wound element cell stack" such that the anode is on the outside of the roll to make electrical contact with the cell case in a case-negative configuration. Using suitable top and bottom insulators, the wound cell stack is inserted into a metallic case of a suitable size dimension. The metallic case may comprise materials such as stainless steel, mild steel, nickel-plated mild steel, titanium, tantalum or aluminum, but not limited thereto, so long as the metallic material is compatible for use with components of the cell.

The cell header comprises a metallic disc-shaped body with a first hole to accommodate a glass-to-metal seal/terminal pin feedthrough and a second hole for electrolyte filling. The glass used is of a corrosion resistant type having up to about 50% by weight silicon such as CABAL 12, TA 23, FUSITE 425 or FUSITE 435. The positive terminal pin feedthrough preferably comprises titanium although molybdenum, aluminum, nickel alloy, or stainless steel can also be used. The cell header is typically of a material similar to that of the case. The positive terminal pin supported in the glass-to-metal seal is, in turn, supported by the header, which is welded to the case containing the electrode assembly. The cell is thereafter filled with the electrolyte solution described hereinabove and hermetically sealed such as by close-welding a stainless steel ball over the fill hole, but not limited thereto.

As is well known to those skilled in the art, the exemplary electrochemical systems of the present invention can also be constructed in case-positive configuration.

As previously described, the present cells are particularly useful for powering implantable medical devices such as cardiac defibrillators, cardiac pacemakers, nerve stimulators, drug pumps, and the like. As is well known by those skilled in the art, an implantable cardiac defibrillator is a device that requires a power source for a generally medium rate, constant resistance load component provided by circuits performing such functions as, for example, the heart sensing and pacing functions. This medical device monitoring function requires electrical current of about 1 microampere to about 100 milliamperes. From time-to-time, the cardiac defibrillator may require a generally high rate, pulse discharge load component that occurs, for example, during charging of a capacitor in the defibrillator for the purpose of delivering an electrical shock to the heart to treat tachyarrhythmias, the irregular, rapid heartbeats that can be fatal if left uncorrected. This medical device operating function requires electrical current of about 1 ampere to about 4 amperes.

As used herein, the term "pulse" means a short burst of electrical current of a significantly greater amplitude than that of a pre-pulse current immediately prior to the pulse. A pulse train consists of at least two pulses of electrical current delivered in relatively short succession with or without open circuit rest between the pulses.

In that respect, an important aspect of the present invention is that during the medical device monitoring function, i.e., during the medium rate discharge, the first and second cathode structures are in equilibrium as the first and second cathode active materials are both discharging at about the same rate or equally sharing the current load. However, during the medical device operating function, i.e., during the high rate, pulse discharge, only the exemplary SVO as the first cathode active material in both the first and second cathode structures is discharged. Then, when the cell returns to the medical device monitoring function, the exemplary $CF_x$ as the second cathode active material serves to re-charge the SVO material of the energy lost of spent during the medical device operating function. This charging continues until the first and second cathode active materials are at an equilibrated voltage. Consequently, if the cell is subjected to an extended period of relative high current discharge above that required for the device monitoring function, the first and second cathode structure having imbalanced percentages of the first and second cathode active materials are in an unbalanced state until such time as the current load decreases to that at which the $CF_x$ material is capable of re-charging the SVO material.

It is appreciated that various modifications to the inventive concepts described herein may be apparent to those of ordinary skill in the art without departing from the spirit and scope of the present invention as defined by the appended claims.

What is claimed is:

1. An electrochemical cell, which comprises:
   a) an anode;
   b) a cathode of a first cathode structure short circuited with a second cathode structure, wherein the first cathode structure comprises a first cathode active material in a first percentage of $(100-x)\%$ and a second cathode active material in a second percentage of $x\%$ and the second cathode structure comprises the first cathode active material in a third percentage of $(100-y)\%$ and the second cathode active material in a fourth percentage of $y\%$, by weight, wherein the ratio of x to y in the first and second cathode structures is selected from the group consisting of $x<y$, $y<x$ and $x=y$, but not $x=y=0$ and wherein the first cathode active material is different than the second cathode active material, the first cathode active material being of a first energy density and a first rate capability and the second cathode active material being of a second energy density and a second rate capability, and wherein the first energy density of the first cathode active material is less than the second energy density while the first rate capability is greater than the second rate capability of the second cathode active material; and
   c) an electrolyte activating the anode and the cathode.

2. The electrochemical cell of claim 1 wherein the anode is of an alkali metal.

3. The electrochemical cell of claim 1 wherein the first and second cathode active materials are selected from the group consisting of silver vanadium oxide, copper silver vanadium oxide, $V_2O_5$, $MnO_2$, $LiCoO_2$, $LiNiO_2$, $LiMnO_2$, $CuO_2$, $TiS_2$, $Cu_2S$, $FeS$, $FeS_2$, $CFx$, $Ag_2O$, $Ag_2O_2$, $CuF$, $Ag_2CrO_4$, $MnO_2$, copper oxide, copper vanadium oxide, and mixtures thereof.

4. The electrochemical cell of claim 1 wherein the cathode has the configuration, by weight: $(100-y)\%$ first cathode active material+$y\%$ second cathode active material, wherein $0<y<100$/current collector/$(100-x)\%$ first cathode active material+$x\%$ second cathode active material, wherein $0<x<100$/current collector/$(100-y)\%$ first cathode active material+$y\%$ second cathode active material, wherein $0<y<100$, and wherein the ratio of x to y is selected from the group consisting of $y<x$, $x<y$ and $x=y$.

5. The electrochemical cell of claim 1 wherein the cathode has the configuration, by weight: $(100-y)\%$ first cathode active material+$y\%$ second cathode active material, wherein $0<y<100$/current collector/$(100-y)\%$ first cathode active material+$y\%$ second cathode active material, wherein $0<y<100/(100-x)\%$ first cathode active material+$x\%$ second cathode active material, wherein $0<x<100/(100-y)\%$ first cathode active material+$y\%$ second cathode active material, wherein $0<y<100$/current collector/$(100-y)\%$ first cathode active material+$y\%$ second cathode active material, wherein $0<y<100$, and wherein the ratio of x to y is selected from the group consisting of $y<x$, $x<y$ and $x=y$.

6. The electrochemical cell of claim 1 wherein the cathode has the configuration, by weight: $(100-y)\%$ first cathode active material+$y\%$ second cathode active material/current collector/$(100-x)\%$ first cathode active material+$x\%$ second cathode active material, wherein the ratio of x to y is selected from the group consisting of $y<x$, $x<y$ and $x=y$, but not $x=y=0$.

7. The electrochemical cell of claim 1 wherein the cathode has the configuration, by weight: $(100-y)\%$ silver vanadium oxide+$y\%$ $CF_x$, wherein $0<y<100$/current collector/$(100-x)\%$ silver vanadium oxide+$x\%$ $CF_x$, wherein $0<x<100$/current collector/$(100-y)\%$ silver vanadium oxide+$y\%$ $CF_x$, wherein $0<y<100$, and wherein the ratio of x to y is selected from the group consisting of $y<x$, $x<y$ and $x=y$.

8. The electrochemical cell of claim 1 wherein the cathode has the configuration, by weight: $(100-y)\%$ silver vanadium oxide+$y\%$ $CF_x$, wherein $0<y<100$/current collector/$(100-y)\%$ silver vanadium oxide+$y\%$ $CF_x$, wherein $0<y<100/(100-x)\%$ silver vanadium oxide+$x\%$ $CF_x$, wherein $0<x<100/(100-y)\%$ silver vanadium oxide+$y\%$ $CF_x$, wherein $0<y<100$/current collector/$(100-y)\%$ silver vanadium oxide+$y\%$ $CF_x$, wherein $0<y<100$, and wherein the ratio of x to y is selected from the group consisting of $y<x$, $x<y$ and $x=y$.

9. The electrochemical cell of claim 1 wherein the anode is lithium and the cathode has the configuration, by weight: $(100-y)\%$ silver vanadium oxide+$y\%$ $CF_x$/current collector/$(100-x)\%$ silver vanadium oxide+$x\%$ $CF_x$, wherein $y<x$ with the $(100-y)\%$ silver vanadium oxide+$y\%$ $CF_x$ facing the lithium anode.

10. The electrochemical cell of claim 1 wherein the anode is lithium and the cathode has the configuration, by weight: $(100-y)\%$ silver vanadium oxide+$y\%$ $CF_x$/current collector/$(100-x)\%$ silver vanadium oxide+$x\%$ $CF_x$, wherein $x<y$ with the $(100-y)\%$ silver vanadium oxide+$y\%$ $CF_x$ facing the lithium anode.

11. An electrochemical cell, which comprises:
   a) an anode;
   b) a cathode of a first cathode structure sandwiched between a first and second current collectors with a second cathode structure contacting at least one of the current collectors opposite the first cathode structure and facing the anode, wherein the first cathode structure comprises a first cathode active material in a first percentage of (100−x)% and a second cathode active material in a second percentage of x% and the second cathode structure comprises the first cathode active material in a third percentage of (100−y)% and the second cathode active material in a fourth percentage of y%, by weight, wherein the ratio of x to y in the first and second cathode structures is selected from the group consisting of x<y, y<x and x=y, but not x=y=0 and wherein the first cathode active material is different than the second cathode active material, the first cathode active material being of a first energy density and a first rate capability and the second cathode active material being of a second energy density and a second rate capability, and wherein the first energy density of the first cathode active material is less than the second energy density while the first rate capability is greater than the second rate capability of the second cathode active material; and c) an electrolyte activating the anode and the cathode.

12. The electrochemical cell of claim 11 wherein the anode is of an alkali metal and the electrolyte is of a nonaqueous chemistry.

13. The electrochemical cell of claim 11 wherein the cathode has the configuration, by weight: (100−y)% first cathode active material+y% second cathode active material, wherein 0<y<100/first current collector/(100−x)% first cathode active material+x% second cathode active material, wherein 0<x<100/second current collector/(100−y)% first cathode active material+y% second cathode active material, wherein 0<y<100, and wherein the ratio of x to y is selected from the group consisting of y<x, x<y and x=y.

14. The electrochemical cell of claim 11 wherein the cathode has the configuration, by weight: (100−y)% silver vanadium oxide+y% $CF_x$, wherein 0<y<100/first current collector/(100−x)% silver vanadium oxide+x% $CF_x$, wherein 0<x<100/second current collector/(100−y)% silver vanadium oxide+y% $CF_x$, wherein 0<y<100, and wherein the ratio of x to y is selected from the group consisting of y<x, x<y and x=y.

15. The electrochemical cell of claim 11 wherein the cathode has the configuration, by weight: (100−y)% silver vanadium oxide+y% $CF_x$, wherein 0<y<100/first current collector/(100−y)% silver vanadium oxide+y% $CF_x$, wherein 0<y<100/(100−x)% silver vanadium oxide+x% $CF_x$, wherein 0<x<100/(100−y)% silver vanadium oxide+y% $CF_x$, wherein 0<y<100/second current collector/(100−y)% silver vanadium oxide+y% $CF_x$, wherein 0<y<100, and wherein the ratio of x to y is selected from the group consisting of y<x, x<y and x=y.

16. The electrochemical cell of claim 11 wherein the anode is lithium and the cathode has the configuration, by weight: (100−y)% silver vanadium oxide+y% $CF_x$/current collector/(100−x)% silver vanadium oxide+x% $CF_x$, wherein y<x with the (100−y)% silver vanadium oxide+y% $CF_x$ facing the lithium anode.

17. The electrochemical cell of claim 11 wherein the anode is lithium and the cathode has the configuration, by weight: (100−y)% silver vanadium oxide+y% $CF_x$/current collector/(100−x)% silver vanadium oxide+x% $CF_x$, wherein x<y with the (100−y)% silver vanadium oxide+y% $CF_x$ facing the lithium anode.

18. The electrochemical cell of claim 11 wherein a third cathode structure contacts the second current collector spaced from the second cathode structure with the first cathode structure intermediate the first and second current collectors, and wherein the third cathode structure comprises the first cathode active material in a fifth percentage of (100−z)% and the second cathode active material in a sixth percentage of z%, and wherein, by weight, y<x and z<x, and wherein y<z or y<z.

19. The electrochemical cell of claim 18 wherein the cathode has the configuration, by weight: (100−y)% first cathode active material+y% second cathode active material, wherein 0<y<100/first current collector/(100−x)% first cathode active material+x% second cathode active material, wherein 0<x<100/second current collector/(100−z)% first cathode active material+z% second cathode active material, wherein 0<z<100, and wherein y<x and z<x and wherein the ratio of y to z is selected from the group consisting of y<z, y>z and y=z.

20. The electrochemical cell of claim 18 wherein the cathode has the configuration, by weight: (100−y)% silver vanadium oxide+y% $CF_x$, wherein 0<y<100/first current collector/(100−x)% silver vanadium oxide+x% $CF_x$, wherein 0<x<100/second current collector/(100−z)% silver vanadium oxide+z% $CF_x$, wherein 0<z<100, and wherein y<x and z<x, and wherein the ratio of y to z is selected from the group consisting of y<z, y>z and y=z.

21. The electrochemical cell of claim 11 wherein the cathode has the configuration, by weight: (100−y)% first cathode active material+y% second cathode active material, wherein 0<y<100/first current collector/(100−y)% first cathode active material+y% second cathode active material, wherein 0<y<100/(100−x)% first cathode active material+x% second cathode active material, wherein 0<x<100/(100−y)% first cathode active material+y% second cathode active material, wherein 0<y<100/second current collector/(100−y)% first cathode active material+y% second cathode active material, wherein 0<y<100, and wherein the ratio of x to y is selected from the group consisting of y<x, x<y and x=y.

22. The electrochemical cell of claim 11 wherein the cathode has the configuration, by weight: (100−y)% first cathode active material+y% second cathode active material, wherein 0<y<100/first current collector/(100−y)% first cathode active material+y% second cathode active material, wherein 0<y<100/(100−x)% first cathode active material+x% second cathode active material, wherein 0<x<100/(100−z)% first cathode active material+z% second cathode active material, wherein 0<z<100/second current collector/(100−z)% first cathode active material+z% second cathode active material, wherein 0<z<100, and wherein y<x and z<x and wherein the ratio of y to z is selected from the group consisting of y<z, y<z and y=z.

23. The electrochemical cell of claim 22 wherein the cathode has the configuration, by weight: (100−y)% silver vanadium oxide+y% $CF_x$, wherein 0<y<100/first current collector/(10−y)% silver vanadium oxide+y% $CF_x$, wherein 0<y<100/(100−x)% silver vanadium oxide+x% $CF_x$, wherein 0<x<100/(100−z)% silver vanadium oxide+z% $CF_x$, wherein 0<z<100/second current collector/100−z)% silver vanadium oxide+z% $CF_x$, wherein 0<z<100, and wherein y<x and z<x, and wherein the ratio of y to z is selected from the group consisting of y<z, y<z and y=z.

24. The electrochemical cell of claim 11 wherein the first and second current collectors are selected from the group consisting of stainless steel, titanium, tantalum, platinum, gold, aluminum, cobalt nickel alloys, highly alloyed ferritic stainless steel containing molybdenum and chromium, and nickel-, chromium-, and molybdenum-containing alloys.

25. The electrochemical cell of claim 11 wherein the first and second current collectors are titanium having a coating selected from the group consisting of graphite/carbon material, iridium, iridium oxide and platinum provided thereon.

26. The electrochemical cell of claim 11 wherein the anode is lithium, the first cathode active material is silver vanadium oxide, the second cathode active material is $CF_x$ and the first and second current collectors are titanium.

27. The electrochemical cell of claim 11 wherein the first and second cathode active materials are selected from the group consisting of silver vanadium oxide, copper silver vanadium oxide, $V_2O_5$, $MnO_2$, $LiCoO_2$, $LiNiO_2$, $LiMnO_2$, $CuO_2$, $TiS_2$, $Cu_2S$, FeS, $FeS_2$, $CF_x$, $Ag_2O$, $Ag_2O_2$, CuF, $Ag_2CrO_4$, copper oxide, copper vanadium oxide, and mixtures thereof.

28. The electrochemical cell of claim 11 wherein the electrolyte is of a nonaqueous chemistry having a first solvent selected from an ester, a linear ether, a cyclic ether, a dialkyl carbonate, and mixtures thereof, and a second solvent selected from a cyclic carbonate, a cyclic ester, a cyclic amide, and mixtures thereof.

29. The electrochemical cell of claim 28 wherein the first solvent is selected from the group consisting of tetrahydrofuran, methyl acetate, diglyme, trigylme, tetragylme, dimethyl carbonate, 1,2-dimethoxyethane, 1,2-diethoxyethane, 1-ethoxy,2-methoxyethane, ethyl methyl carbonate, methyl propyl carbonate, ethyl propyl carbonate, diethyl carbonate, dipropyl carbonate, and mixtures thereof, and the second solvent is selected from the group consisting of propylene carbonate, ethylene carbonate, butylene carbonate, acetonitrile, dimethyl sulfoxide, dimethyl formamide, dimethyl acetamide, γ-valerolactone, γ-butyrolactone, N-methylpyrrolidinone, and mixtures thereof.

30. The electrochemical cell of claim 11 wherein the electrolyte includes a lithium salt selected from the group consisting of $LiPF_6$, $LiBF_4$, $LiAsF_6$, $LiSbF_6$, $LiClO_4$, $LiO_2$, $LiAlCl_4$, $LiGaCl_4$, $LiC(SO_2CF_3)_3$, $LiN(SO_2CF_3)_2$, LiSCN, $LiO_3SCF_2$, $LiC_6F_5SO_3$, $LiO_2CCF_3$, $LiSO_6F$, $LiB(C_6H_5)_4$, $LiCF_3SO_3$, and mixtures thereof.

31. The electrochemical cell of claim 11 wherein the electrolyte is 0.8M to 1.5M $LiAsF_6$ or $LiPF_6$ dissolved in a 50:50 mixture, by volume, of propylene carbonate as the first solvent and 1,2-dimethoxyethane as the second solvent.

32. An electrochemical cell, which comprises:
a) an anode;
b) a cathode of a first cathode structure and a second cathode structure, wherein the first cathode structure has spaced apart first and second major sides with at least one current collector contacting at least one of the first and second major sides and wherein the second cathode structure is contacted to the at least one current collector opposite the first cathode structure and facing the anode, wherein the first cathode structure comprises a first cathode active material of a first energy density and a first rate capability present in a first percentage of (100−x)% and a second cathode active material of a second energy density and a second rate capability present in a second percentage of x% and the second cathode structure comprises the first cathode active material in a third percentage of (100−y)% and the second cathode active material in a fourth percentage of y%, by weight, wherein the first cathode active material is different than the second cathode active material with y≦x, but not x=y=0, and wherein the first energy density of the first cathode active material is less than the second energy density while the first rate capability is greater than the second rate capability of the second cathode active material; and c) a nonaqueous electrolyte activating the anode and the cathode.

33. The electrochemical cell of claim 32 wherein the cathode has the configuration, by weight: (100−y)% first cathode active material+y% second cathode active material/current collector/(100−x)% first cathode active material+x% second cathode active material.

34. The electrochemical cell of claim 32 wherein the anode is lithium and the cathode has the configuration, by weight: (100−y)% silver vanadium oxide+y% $CF_x$/current collector/(100−x)% silver vanadium oxide+x% $CF_x$, wherein y<x with the (100−y)% silver vanadium oxide+y% $CF_x$ facing the lithium anode.

35. The electrochemical cell of claim 32 wherein the anode is lithium and the cathode has the configuration, by weight: (100−y)% silver vanadium oxide+y% $CF_x$/current collector/(100−x)% silver vanadium oxide+x% $CF_x$, wherein x<y with the (100−y)% silver vanadium oxide+y% $CF_x$ facing the lithium anode.

36. The electrochemical cell of claim 32 wherein the first and second cathode active materials are selected from the group consisting of silver vanadium oxide, copper silver vanadium oxide, $V_2O_5$, $MnO_2$, $LiCoO_2$, $LiNiO_2$, $LiMnO_2$, $CuO_2$, $TiS_2$, $Cu_2S$, Fes, $FeS_2$, $CF_x$, $Ag_2O$, $Ag_2O_2$, CuF, $Ag_2CrO_4$, copper oxide, copper vanadium oxide, and mixtures thereof.

37. The electrochemical cell of claim 32 wherein the current collectors are selected from the group consisting of stainless steel, titanium, tantalum, platinum, gold, aluminum, cobalt nickel alloys, highly alloyed ferritic stainless steel containing molybdenum and chromium, and nickel-, chromium-, and molybdenum-containing alloys.

38. In combination with an implantable medical device requiring a substantially constant discharge current during a medical device monitoring function and at least one current pulse discharge for a medical device operating function, an electrochemical cell, which comprises:
a) an anode;
b) a cathode of a first cathode structure sandwiched between a first and second current collectors with a second cathode structure contacting at least one of the current collectors opposite the first cathode structure and facing the anode, wherein the first cathode structure comprises a first cathode active material in a first percentage of (100−x)% and a second cathode active material in a second percentage of x% and the second cathode structure comprises the first cathode active material in a third percentage of (100−y)% and the second cathode active material in a fourth percentage of y%, by weight, wherein the ratio of x to y in the first and second cathode structures is selected from the group consisting of x<y, y<x and x=y, but not x=y=0 and wherein the first cathode active material is different than the second cathode active material, the first cathode active material being of a first energy density and a first rate capability and the second cathode active material being of a second energy density and a second rate capability, and wherein the first energy density of the first cathode active material is less than the second energy density while the first rate capability is greater than the second rate capability of the second cathode active material; and
c) an electrolyte activating the anode and the cathode.

39. The combination of claim 38 wherein the medical device monitoring function requires electrical current of about 1 microampere to about 100 milliamperes, and wherein the medical device operating function requires current of about 1 ampere to about 4 amperes.

40. The combination of claim 38 wherein the medical device monitoring function is provided by both the first and the second cathode active materials of the first and second cathode structures.

41. The combination of claim 38 wherein the medical device operating function is substantially provided by the first cathode active material having a first energy density and a first rate capability in comparison to the second cathode active material having a second energy density and a second rate capability, wherein the second energy density is greater than the first energy density and the first rate capability is greater than the second rate capability.

42. A method for providing an electrochemical cell, comprising the steps of:
   a) providing an anode;
   b) providing a cathode of a first cathode structure short circuited with a second cathode structure, wherein the first cathode structure comprises a first cathode active material in a first percentage of $(100-x)\%$ and a second cathode active material in a second percentage of $x\%$ and the second cathode structure comprises the first cathode active material in a third percentage of $(100-y)\%$ and the second cathode active material in a fourth percentage of $y\%$, by weight, wherein the ratio of x to y in the first and second cathode structures is selected from the group consisting of $x<y$, $y<x$ and $x=y$, but not $x=y=0$ and wherein the first cathode active material is different than the second cathode active material, the first cathode active material being of a first energy density and a first rate capability and the second cathode active material being of a second energy density and a second rate capability, and wherein the first energy density of the first cathode active material is less than the second energy density while the first rate capability is greater than the second rate capability of the second cathode active material; and
   c) activating the anode and cathode with a nonaqueous electrolyte.

43. The method of claim 42 including selecting the first and second cathode active materials from the group consisting of silver vanadium oxide, copper silver vanadium oxide, $V_2O_5$, $MnO_2$, $LiCoO_2$, $LiNiO_2$, $LiMnO_2$, $CuO_2$, $TiS_2$, $Cu_2S$, $FeS$, $FeS_2$, $CF_x$, $Ag_2O$, $Ag_2O_2$, $CuF$, $Ag_2CrO_4$, $MnO_2$, copper oxide, copper vanadium oxide, and mixtures thereof.

44. The method of claim 42 including providing the cathode having the configuration, by weight: $(100-y)\%$ first cathode active material+$y\%$ second cathode active material, wherein $0<y<100$/current collector/$(100-x)\%$ first cathode active material+$x\%$ second cathode active material, wherein $0<x<100$/current collector/$(100-y)\%$ first cathode active material+$y\%$ second cathode active material, wherein $0<y<100$, and wherein the ratio of x to y is selected from the group consisting of $y<x$, $x<y$ and $x=y$.

45. The method of claim 42 including providing the cathode having the configuration, by weight: $(100-y)\%$ first cathode active material+$y\%$ second cathode active material, wherein $0<y<100$/current collector/$(100-y)\%$ first cathode active material+$y\%$ second cathode active material, wherein $0<y<100$/$(100-x)\%$ first cathode active material+$x\%$ second cathode active material, wherein $0<x<100$/$(100-y)\%$ first cathode active material+$y\%$ second cathode active material, wherein $0<y<100$/current collector/$(100-y)\%$ first cathode active material+$y\%$ second cathode active material, wherein $0<y<100$, and wherein the ratio of x to y is selected from the group consisting of $y<x$, $x<y$ and $x=y$.

46. The method of claim 42 including providing the cathode having the configuration, by weight: $(100-y)\%$ first cathode active material+$y\%$ second cathode active material/current collector/$(100-x)\%$ first cathode active material+$x\%$ second cathode active material.

47. The method of claim 42 including providing the cathode having the configuration, by weight: $(100-y)\%$ SVO+$y\%$ $CF_x$, wherein $0<y<100$/current collector/$(100-x)\%$ SVO+$x\%$ $CF_x$, wherein $0<x<100$/current collector/$(100-y)\%$ SVO+$y\%$ $CF_x$, wherein $0<y<100$, and wherein the ratio of x to y is selected from the group consisting of $y<x$, $x<y$ and $x=y$.

48. The method of claim 42 including providing the cathode having the configuration, by weight: $(100-y)\%$ silver vanadium oxide+$y\%$ $CF_x$, wherein $0<y<100$/current collector/$(100-y)\%$ silver vanadium oxide+$y\%$ $CF_x$, wherein $0<y<100$/$(100-x)\%$ silver vanadium oxide+$x\%$ $CF_x$, wherein $0<x<100$/$(100y)\%$ silver vanadium oxide+$y\%$ $CF_x$, wherein $0<y<100$/current collector/$(100-y)\%$ silver vanadium oxide+$y\%$ $CF_x$, wherein $0<y<100$, and wherein the ratio of x to y is selected from the group consisting of $y<x$, $x<y$ and $x=y$.

49. The method of claim 42 including providing the anode of lithium and the cathode having the configuration, by weight: $(100-y)\%$ silver vanadium oxide+$y\%$ $CF_x$/current collector/$(100-x)\%$ silver vanadium oxide+$x\%$ $CF_x$, wherein $y<x$ with the $(100-y)\%$ silver vanadium oxide+$y\%$ $CF_x$ facing the lithium anode.

50. The method of claim 42 including providing the anode of lithium and the cathode having the configuration, by weight: $(100-y)\%$ silver vanadium oxide+$y\%$ $CF_x$/current collector/$(100-x)\%$ silver vanadium oxide+$x\%$ $CF_x$, wherein $x<y$ with the $(100-y)\%$ SVO+$y\%$ $CF_x$ facing the lithium anode.

* * * * *

UNITED STATES PATENT AND TRADEMARK OFFICE
CERTIFICATE OF CORRECTION

PATENT NO. : 6,692,865 B2  Page 1 of 1
DATED : February 17, 2004
INVENTOR(S) : Gan et al.

It is certified that error appears in the above-identified patent and that said Letters Patent is hereby corrected as shown below:

Column 12,
Lines 49 and 59, "y<z" should be -- y>z --

Column 13,
Line 16, "nonaquecus" should be -- nonaqueous --

Column 16,
Line 33, "(100y)" should be -- (100-y) --

Signed and Sealed this

Twenty-fifth Day of May, 2004

JON W. DUDAS
*Acting Director of the United States Patent and Trademark Office*